(12) United States Patent
Collins et al.

(10) Patent No.: US 10,905,544 B2
(45) Date of Patent: Feb. 2, 2021

(54) INTRAOCULAR LENSES HAVING CLOSED-LOOP RING HAPTIC STRUCTURES

(71) Applicant: Alcon Inc., Fribourg (CH)

(72) Inventors: Stephen John Collins, Fort Worth, TX (US); Jian Liu, Keller, TX (US); Michael Lee Mangum, Lake Forest, CA (US); Douglas Brent Wensrich, Bedford, TX (US)

(73) Assignee: Alcon Inc., Fribourg (CH)

( * ) Notice: Subject to any disclaimer, the term of this patent is extended or adjusted under 35 U.S.C. 154(b) by 127 days.

(21) Appl. No.: 16/144,570

(22) Filed: Sep. 27, 2018

(65) Prior Publication Data

US 2019/0091010 A1 Mar. 28, 2019

Related U.S. Application Data

(60) Provisional application No. 62/564,001, filed on Sep. 27, 2017.

(51) Int. Cl.
*A61F 2/16* (2006.01)

(52) U.S. Cl.
CPC .............. *A61F 2/1613* (2013.01); *A61F 2/16* (2013.01); *A61F 2/1694* (2013.01); *A61F 2002/169* (2015.04); *A61F 2002/1681* (2013.01); *A61F 2002/16901* (2015.04)

(58) Field of Classification Search
CPC ........ A61F 2/1613; A61F 2/16; A61F 2/1694; A61F 2/16901; A61F 2/169; A61F 2002/16901; A61F 2002/169; A61F 2002/1681

See application file for complete search history.

(56) References Cited

U.S. PATENT DOCUMENTS

| 8,585,759 B2* | 11/2013 | Bumbalough | A61F 2/1694 623/6.37 |
| 2009/0012609 A1* | 1/2009 | Geraghty | A61F 2/1635 623/6.11 |

* cited by examiner

*Primary Examiner* — David H Willse
*Assistant Examiner* — Tiffany P Shipmon

(57) ABSTRACT

An ophthalmic device includes an optic including an optic axis and a periphery and a closed-loop ring haptic structure coupled with the optic. The closed loop haptic structure includes a first ring structure having a first characteristic length, a second ring structure having a second characteristic length, and a plurality of connectors coupling the first ring structure and the second ring structure. The first ring structure is positioned adjacent to the periphery of the optic and is coupled to the entire periphery of the optic, and the first characteristic length is less than the second characteristic length.

11 Claims, 7 Drawing Sheets

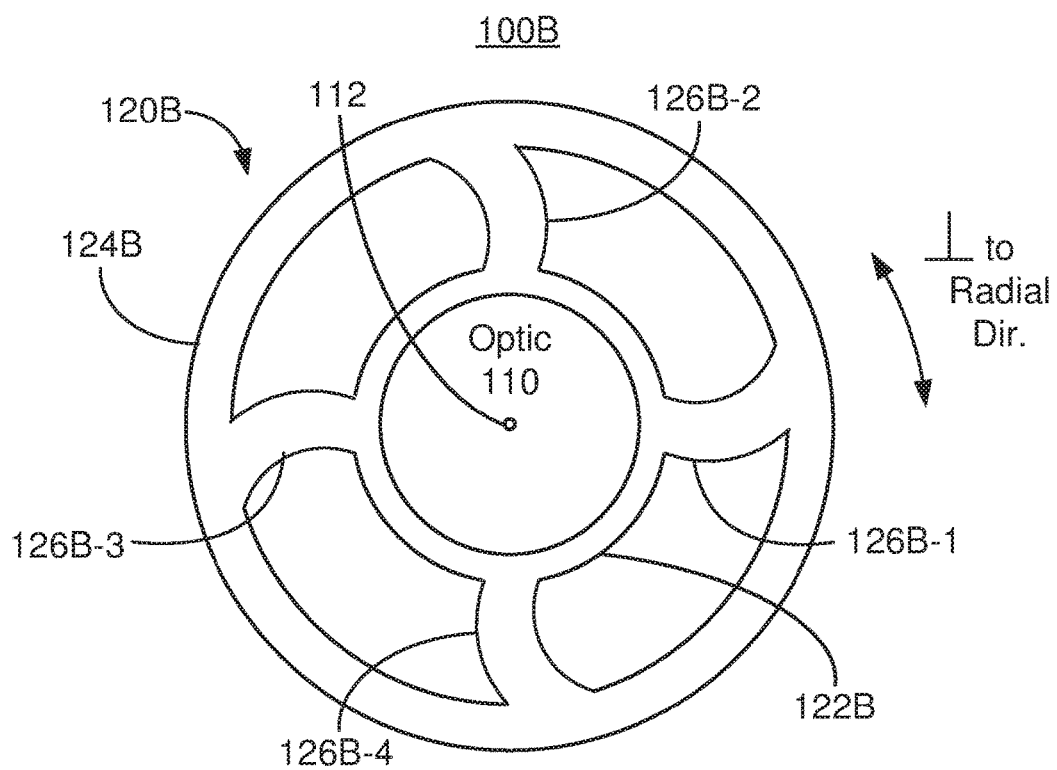
FIG. 2
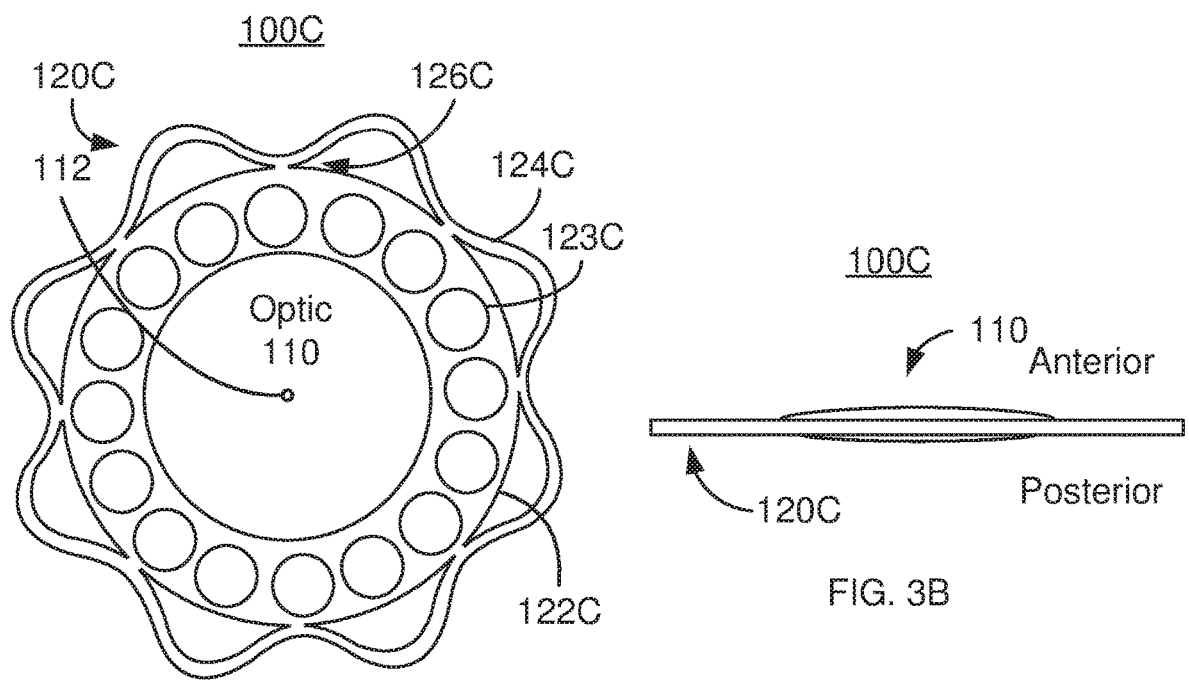
FIG. 3A
FIG. 3B

INTRAOCULAR LENSES HAVING CLOSED-LOOP RING HAPTIC STRUCTURES

FIELD

The present disclosure relates generally ophthalmic lenses and, more particularly, to intraocular lenses having closed-loop ring haptic structures.

BACKGROUND

Intraocular lenses (IOLs) may be implanted in patients' eyes to replace a patient's natural lens. An IOL typically includes (1) an optic that corrects the patient's vision (e.g., typically via refraction or diffraction), and (2) haptics that constitute support structures that hold the optic in place within the patient's eye (e.g., within capsular bag). In general, a physician selects an IOL for which the optic has the appropriate corrective characteristics for the patient. During ophthalmic surgery, often performed for conditions such as cataracts, the surgeon implants selected IOL by making an incision in the capsular bag of the patient's eye (a capsulorhexis) and inserting the IOL through the incision. Typically, the IOL is folded for insertion into the capsular bag via a corneal incision and unfolded once in place within the capsular bag. During unfolding, the haptics may expand such that a small section of each bears on the capsular bag, retaining the IOL in place.

Although existing IOLs may function acceptably well in many patients, they also have certain shortcomings. For example, existing IOL design may include haptics that cause striae, or folds, in the posterior capsular bag. Such striae may result from the haptics having a relatively small angle of contact with the capsular bag. Because striae may negatively impact patient outcomes (e.g., by resulting in increased posterior capsular opacification (PCO) by providing a mechanism for the growth and/or migration of cells), haptic designs that reduce striae are desirable. Moreover, such designs should also have a volume and foldability conducive to maintaining acceptably small incision sizes (e.g., 3 mm or less) as larger incision may adversely affect the patient's recovery.

Accordingly, what is needed is an improved IOL that may address PCO (e.g., by reducing striae) without significantly complicating implantation.

BRIEF SUMMARY OF THE INVENTION

An ophthalmic device includes an optic including an optic axis and a periphery and a closed-loop ring haptic structure coupled with the optic. The closed loop haptic structure includes a first ring structure having a first characteristic length, a second ring structure having a second characteristic length, and a plurality of connectors coupling the first ring structure and the second ring structure. The first ring structure is positioned adjacent to the periphery of the optic and is coupled to the entire periphery of the optic, and the first characteristic length is less than the second characteristic length.

In certain embodiments, the closed-loop haptic structure described herein may result in fewer striae and reduced PCO, yet may be relatively easily implanted. Consequently, performance of the ophthalmic device may be improved.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein:

FIG. 2 depicts another exemplary embodiment of an ophthalmic device having a closed-loop ring haptic structure;

FIGS. 3A-3B depict another exemplary embodiment of an ophthalmic device having a closed-loop ring haptic structure;

The skilled person in the art will understand that the drawings, described below, are for illustration purposes only. The drawings are not intended to limit the scope of the applicant's disclosure in any way.

DETAILED DESCRIPTION

The exemplary embodiments relate to ophthalmic devices such as intraocular lenses (IOLs). The following description is presented to enable one of ordinary skill in the art to make and use the invention and is provided in the context of a patent application and its requirements. Various modifications to the exemplary embodiments and the generic principles and features described herein will be readily apparent. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. Thus, the present invention is not intended to be limited to the embodiments shown, but is to be accorded the widest scope consistent with the principles and features described herein.

In general, the present disclosure relates to an ophthalmic device including an optic including an optic axis and a periphery and a closed-loop ring haptic structure coupled with the optic. The closed loop haptic structure includes a first ring structure having a first characteristic length, a second ring structure having a second characteristic length, and a plurality of connectors coupling the first ring structure and the second ring structure. The first ring structure is positioned adjacent to the periphery of the optic and is coupled to the entire periphery of the optic, and the first characteristic length is less than the second characteristic length.

Figure 1A:
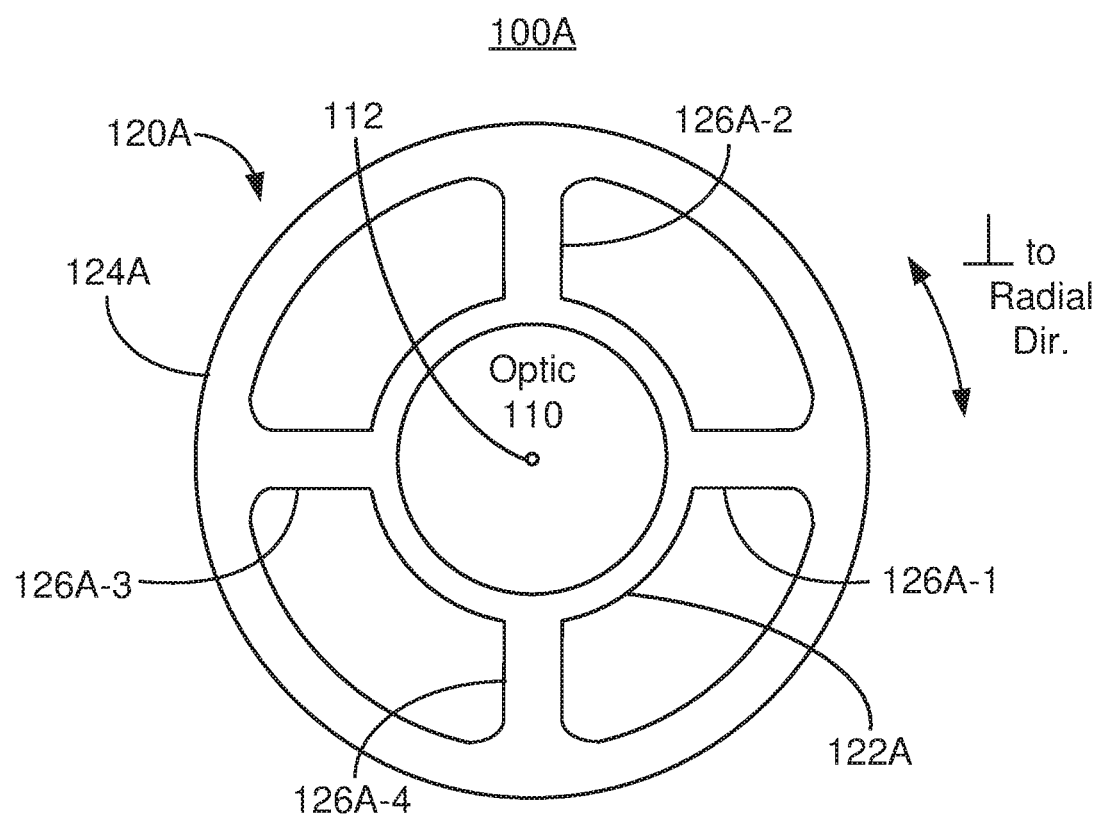
FIGS. 1A-1B depict various views of an exemplary embodiment of an ophthalmic device having a closed-loop haptic structure.
Figure 1B:
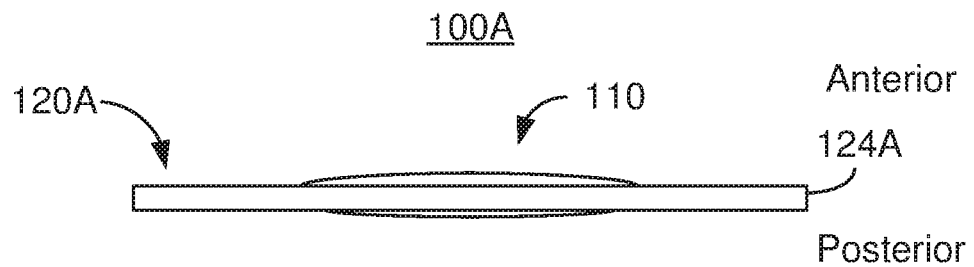

FIGS. 1A-1B depicts an exemplary embodiment of an ophthalmic device 100A having an optic 110 and a closed-loop ring haptic structure 120A. For simplicity, the ophthalmic device 100A is also referred to as an IOL 100A. FIG. 1A depicts a plan view of the IOL 100A, while FIG. 1B depicts a side view of the IOL 100A. For clarity, FIGS. 1A-1B are not to scale and not all components may be shown. In some embodiments, the haptic structure 120A and optic 110 are a single a monolithic structure. In such embodiments, the closed-loop haptic structure 120A and the optic 110 may be molded together. Thus, the optic 110 and haptic 120A may form a single monolithic structure. In other embodiments, the closed-loop ring haptic structure 120A and the optic 110 may be formed separately and may be bonded or otherwise affixed together. In such embodiments, the closed-loop ring haptic structure 120A and optic 110 may be formed of the same or different material(s).

The optic 110 is an ophthalmic lens 110 that may be used to correct a patient's vision. For example, the optic may be a refractive and/or diffractive lens. The optic 110 may be a monofocal lens, multifocal lens and/or a toric lens. The anterior and/or posterior surface of the optic 110 may thus have features including but not limited to a base curvature and diffraction grating(s). The optic 110 may refract and/or diffract light to correct the patient's vision. The optic 110 has an optic axis 112 that is out of the plane of the page but shown as a circle in FIG. 1A. The optic 110 is depicted as having a circular footprint in the plan view of FIG. 1A. In other embodiments, the optic 110 may have a differently shaped footprint. In some embodiments, the optic 110 may also include other features that are not shown. The optic 110 may be formed of one or more of a variety of flexible optical materials. For example, the optic 110 may include but is not limited to one or more of silicone, a hydrogel and an acrylic such as AcrySof®.

The closed-loop ring haptic structure 120A is a support structure used to hold the ophthalmic device 100A in place in the capsular bag of a patient's eye (not explicitly shown). The closed-loop haptic structure 120A includes a first (inner) ring 122A, a second (outer) ring 124A and connectors 126A-1, 126A-2, 126A-3 and 126A-4 (collectively 126A). Connectors 126A are struts that connect the first ring 122A with the second ring 124A. The first ring 122A is adjacent to the periphery of the optic 110. In some embodiments, the first ring 122A adjoins the optic 110. The first ring 122A may be desired to match the shape of the optic 110. Thus, the first ring 122A is shown as a circle having a single characteristic length: the diameter (or radius). In other embodiments, the first ring 122A may have a different shape.

The second ring 124A retains the IOL 100A in position in the patient's eye by contacting the capsular bag. In the embodiment shown, the second ring 124A is a circle and thus has a single characteristic length: the radius (or diameter) of the ring 124A. In other embodiments, the second ring 124A may have a different shape and thus multiple characteristic lengths. The second ring 124A contacts the capsular bag around the entire periphery of the ring 124A. Stated differently, the contact angle subtended by the second ring 124A is three hundred and sixty degrees. As a result, the capsular bag may thus be extended over a large volume, stretching the capsular bag over a larger region than would be the case for an IOL having open loop haptics. This may reduce striae and, therefore, the incidence of PCO.

As can also be seen in FIG. 1B, the closed-loop ring haptic structure 120A includes sharp corners. More specifically, both the first (inner) ring 122A and the second (outer) ring 124A may have sharp corners. As a result, the optic 110 may be surrounded on the sides by sharp edges. These sharp edges may also reduce the probability of cells migrating to the optic 110 from any side, thereby further reducing the incidence of PCO.

Use of the IOL 100A may improve patient outcomes. The second ring 124A allows the closed-loop ring haptic structure 120A to contact a larger portion of and better extend the capsular bag as compared to IOL having alternative haptic designs (e.g., open loop haptics). This may not only improve the axial and rotational stability of the IOL 100A, but also reduce the formation of striae (wrinkles) in the capsular bag. The three-hundred-and-sixty-degree angle of contact with the capsular bag may thus reduce the incidence of PCO. Sharp edges for the closed-loop haptic structure 120A may further reduce PCO. Thus, performance of the IOL 100A may be improved.

FIG. 2 depicts another exemplary embodiment of an ophthalmic device 100B having an optic 110 and a closed-loop ring haptic structure 120B. For simplicity, the ophthalmic device 100B is also referred to as an IOL 100B. The IOL 100B is analogous to the IOL 100A. Consequently, analogous components have similar labels. Thus, the IOL 100B includes an optic 110 and closed-loop ring haptic structure 120B that are analogous to the optic 110 and closed-loop ring haptic structure 120A. Because optic 110 of IOL 100B is substantially the same as the optic 110 of IOL 100A, the optic 110 of IOL 100B will not be separately described with regard to FIG. 2. For clarity, FIG. 2 is not to scale and not all components may be shown.

Like the closed loop haptic structure 120A of IOL 100A, the closed-loop haptic structure 120B of IOL 100B may include a first (inner) ring 122B, a second (outer) ring 124B, and connectors 126B-1, 126B-2, 126B-3 and 126B-4 (collectively 126B).

The primary difference between IOL 100B and IOL 100A (described above) is that, in IOL 100B, connectors 126B are curved. In other words, each of the connectors 126B has a component in the radial direction to connect the rings 122B and 124B and a component perpendicular to the radial direction (i.e. in an angular direction around the circle).

For substantially the same reasons as discussed above with regard to IOL 100A, IOL 100B may improve patient outcomes by reducing incidence of PCO. Additionally, when the second ring 124B is under compression, the curved connectors 126B may be more likely to bend along the curves substantially in the plane of the closed-loop ring haptic 120B. Movement of the optic 110 and/or closed-loop ring haptic structure 120B toward the anterior or posterior of the eye due to compression may be reduced, thereby improving refractive outcomes.

FIGS. 3A-3B depict another exemplary embodiment of an ophthalmic device 100C having an optic 110 and a closed-loop ring haptic structure 120C. For simplicity, the ophthalmic device 100C is also referred to as an IOL 100C. FIG. 3A is a plan view of the IOL 100C, while FIG. 3B is a side view of the IOL 100C. The IOL 100C is analogous to the IOLs 100A. Consequently, analogous components have similar labels. Thus, the IOL 100C includes an optic 110 and closed-loop ring haptic structure 120C that are analogous to the optic 110 and closed-loop haptic structures 120A. Because optic 110 of IOL 100C is substantially the same as the optic 110 of IOL 100A, the optic 110 of IOL 100C will not be separately described with regard to FIG. 3A-3B. For clarity, FIGS. 3A and 3B are not to scale and not all components may be shown.

Like the closed loop haptic structure 120A of IOL 100A, the closed-loop haptic structure 120C of IOL 100C may include a first (inner) ring 122C, a second (outer) ring 124C, and connectors 126C (of which only one is labeled).

The primary differences between IOL 100C and IOL 100A (described above) are as follows. First, the second ring 124C has a wavy periphery and, therefore, multiple characteristic lengths. Although a particular shape is depicted, the present disclosure contemplates that the second ring 124C may have a different shape and other multiple or single characteristic lengths. Second, the first ring 122C may be significantly wider than the ring 122A. In order to ensure that the IOL 100C is still sufficiently compressible, apertures 123C may be been formed in the first ring 122C. Third, the connectors 126C may be the contact points between the first and second rings. In other embodiments, the connectors 126C may be struts or other structures.

The second ring 124C may contact the capsular bag at least at the portions of the periphery of the ring 124C that are furthest from the optical axis 112. Because these portions are oriented around the full three hundred and sixty degrees of the contact angle, the capsular bag is still extended in a similar manner as described above with regard to IOL 100A. Accordingly, IOL 100C may have similar benefits in reducing striae and the incidence of PCO. In certain embodiments, the wavy shape of outer ring 124C may improve the response of IOL 100C to compression, further improving performance.

Figure 4A:
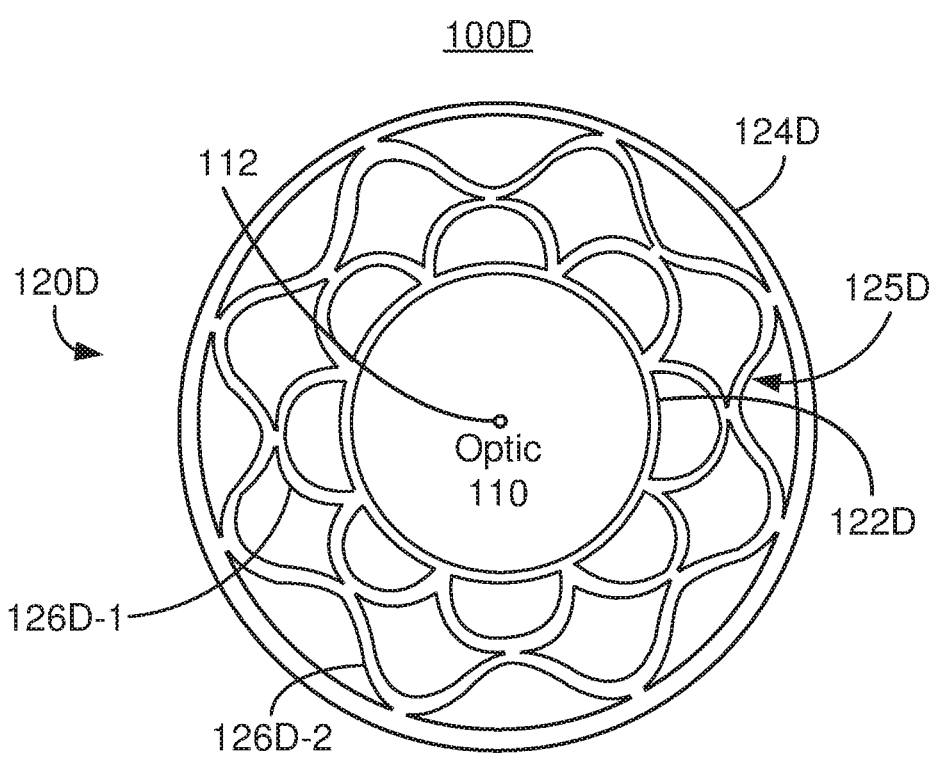
FIGS. 4A-4B depict another exemplary embodiment of an ophthalmic device having a closed-loop ring haptic structure.
Figure 4B:
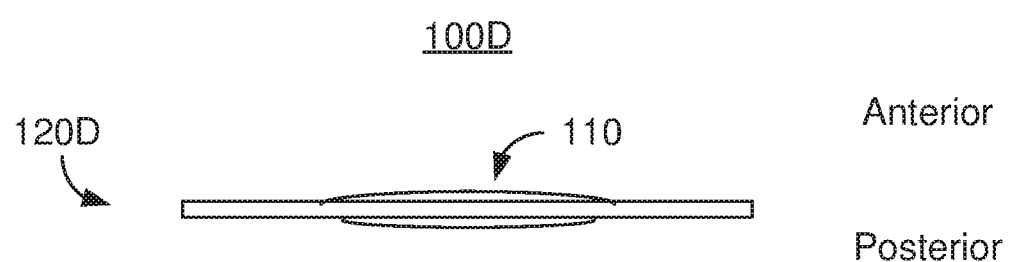

FIGS. 4A-4B depict another exemplary embodiment of an ophthalmic device 100D having an optic 110 and a closed-loop ring haptic structure 120D. For simplicity, the ophthalmic device 100D is also referred to as an IOL 100D. FIG. 4A is a plan view of the IOL 100D, while FIG. 4B is a side view of the IOL 100D. The IOL 100D is analogous to the IOLs 100A. Consequently, analogous components have similar labels. Thus, the IOL 100D includes an optic 110 and closed-loop ring haptic structure 120D that are analogous to the optic 110 and closed-loop haptic structures 120A. Because optic 110 of IOL 100E is substantially the same as the optic 110 of IOL 100A, the optic 110 of IOL 100D will not be separately described with regard to FIGS. 4A-4B. For clarity, FIGS. 4A and 4B are not to scale and not all components may be shown.

Like the closed loop haptic structure 120A of IOL 100A, the closed-loop haptic structure 120D of IOL 100D may include a first (inner) ring 122D, a second (outer) ring 124D, and connectors collectively labeled 126D (of which only one is labeled).

The primary differences between IOL 100D and IOL 100A (described above) is that, in IOL 100D, the connectors 126D include multiple ring structures. In the embodiment shown, the connectors 126D include a first ring structure 126D-1 and a second ring structure 126D-2 (collectively connectors 126D). The first and second ring structures 126D-1 and 126D-2 collectively form multiple points of connection between first ring 122D and second ring 124D. In the depicted embodiment, the first ring structure 126D-1 may be viewed as a set of loops connected with the first ring 122D, while the second ring structure 126D-2 is a wavy structure analogous to the second ring 124C depicted in FIG. 3. In other embodiments, a different number and/or type of ring structure may be used.

For substantially the same reasons as discussed above with regard to IOL 100A, IOL 100D may improve patient outcomes by reducing incidence of PCO. Additionally, forming connectors 126D from ring structures 126D-1 and 126D-2 may improve the compressibility of the IOL 100D for implantation, further improving performance.

Figure 5A:
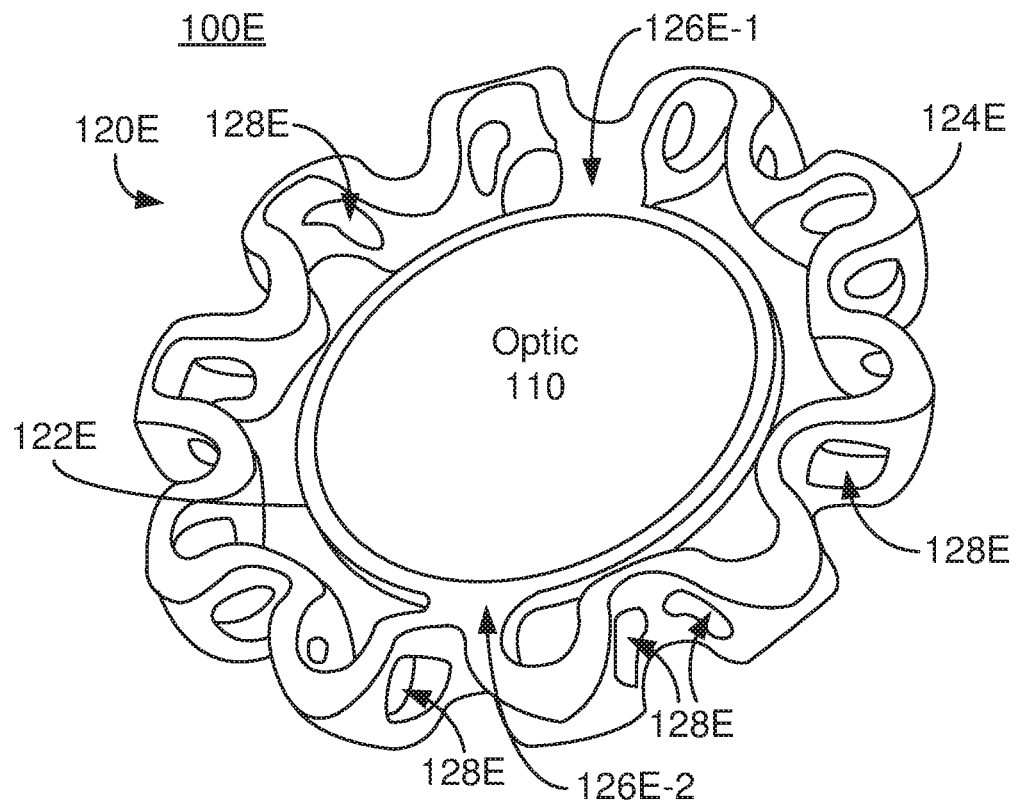
FIGS. 5A-5B depict another exemplary embodiment of an ophthalmic device having a closed-loop ring haptic structure.
Figure 5B:
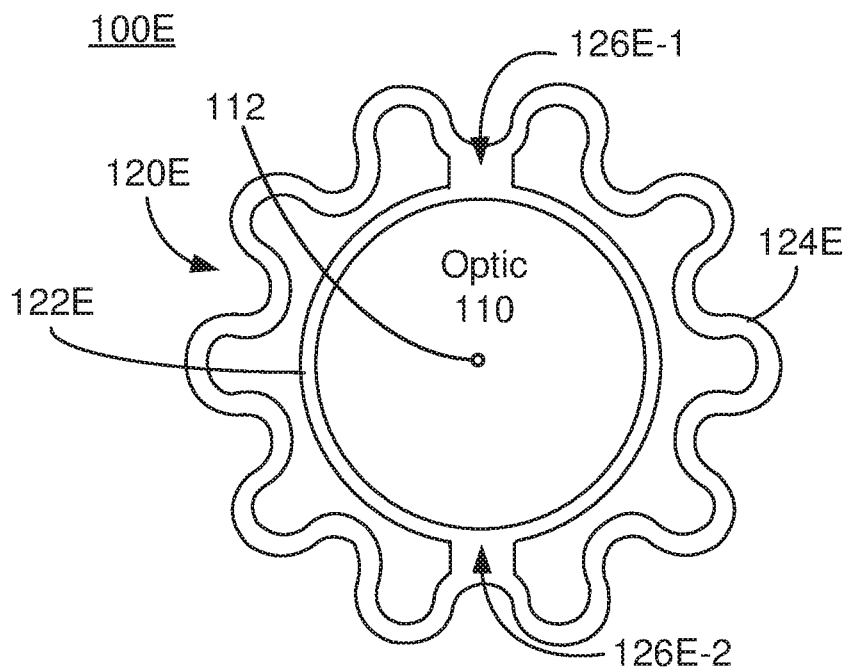

FIGS. 5A-5B depict another exemplary embodiment of an ophthalmic device 100E having an optic 110 and a closed-loop ring haptic structure 120E. For simplicity, the ophthalmic device 100E is also referred to as an IOL 100E. FIG. 5A is a perspective view of the IOL 100E, while FIG. 5B is a plan view of the IOL 100E. The IOL 100E is analogous to IOLs 100A. Consequently, analogous components have similar labels. Thus, the IOL 100E includes an optic 110 and closed-loop ring haptic structure 120E that are analogous to the optic 110 and closed-loop haptic structure 120A. Because optic 110 of IOL 100E is substantially the same as the optic 110 of IOL 100A, the optic 110 of IOL 100E will not be separately described with regard to FIGS. 5A-5B. For clarity, FIGS. 5A and 5B are not to scale and not all components may be shown.

Like the closed loop haptic structure 120A of IOL 100A, the closed-loop haptic structure 120E of IOL 100E may include a first (inner) ring 122E, a second (outer) ring 124E, and connectors 126E-1 and 126E-2 (collectively labeled 126E).

The primary differences between IOL 100E and IOL 100A (described above) are as follows. First, the second ring 124E has a wavy periphery and, therefore, multiple characteristic lengths. Although a particular shape is depicted, the present disclosure contemplates that the second ring 124C may have a different shape and other multiple or single characteristic lengths. Second, the second ring 124E may have a three-dimensional structure in which the thickness of the second ring 124E along the optical axis 112 varies with radial position around the optic 110. Third, the second ring 124E may have one or more apertures 128E formed therein. For clarity, only a few of the apertures 128E are labeled. The apertures 128E may allow the second ring 124E to be more flexible for compression during delivery. For example, the second ring 124E may be compressible in the axial (parallel to the optic axis) and radial (along a radius from the center of the ring 122E/124E) directions.

For substantially the same reasons as discussed above with regard to IOL 100A, IOL 100E may improve patient outcomes by reducing incidence of PCO. Additionally, the second ring 124E, having a three dimensional structure, may hold the capsular bag open in the radial direction as well as providing a wider contact surface in the direction parallel to the optic axis 112. Thus, the striae reduction and PCO prevention benefits may be enhanced.

Figure 6A:
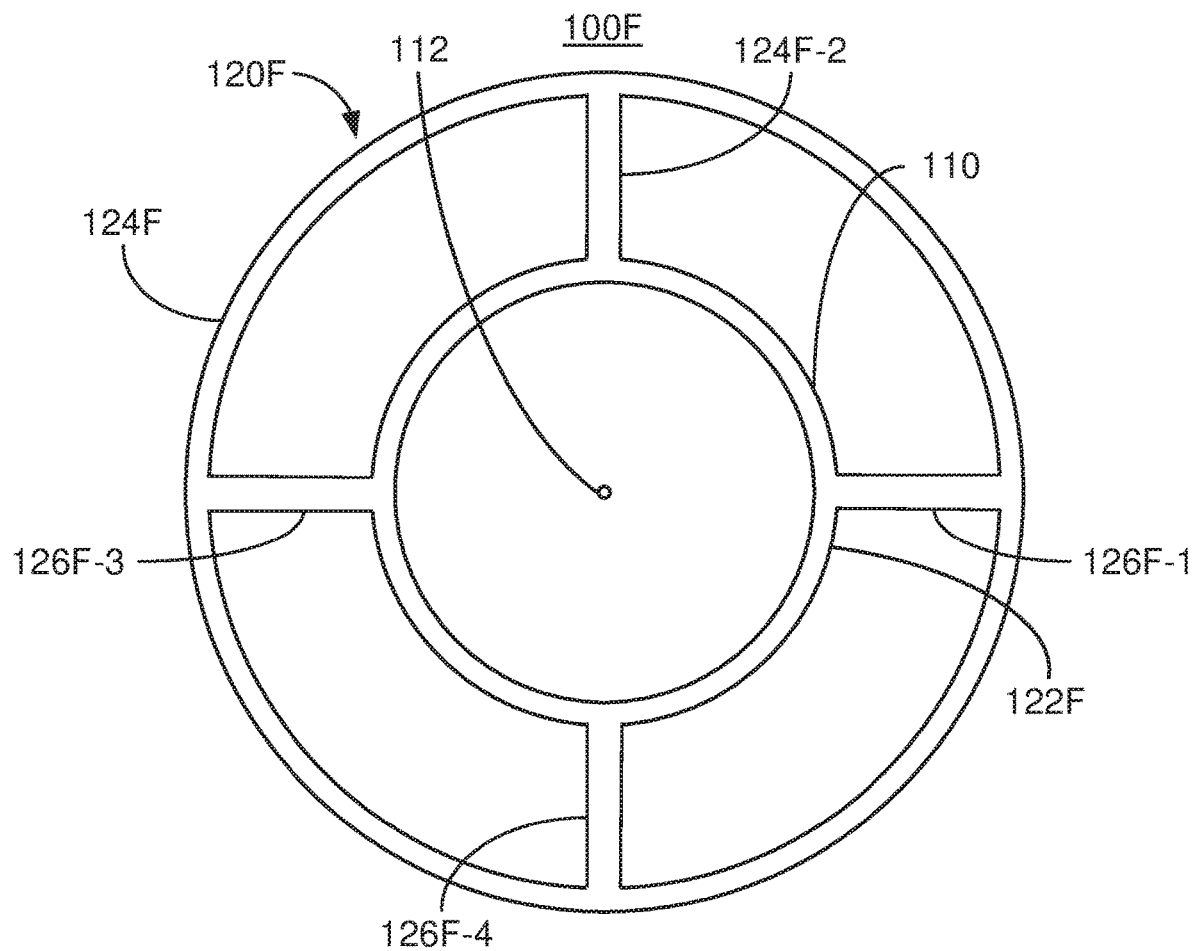
FIGS. 6A-6B depict various views of another exemplary embodiment of an ophthalmic device having a closed-loop ring haptic structure.
Figure 6B:
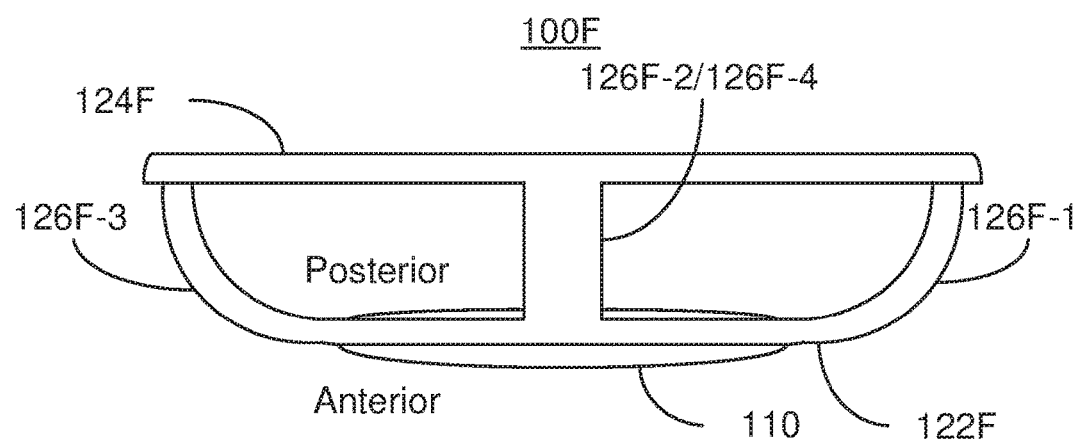

FIGS. 6A and 6B depict plan and side views, respectively, of another exemplary embodiment of an ophthalmic device 100F having an optic 110 and a closed-loop ring haptic structure 120F. For simplicity, the ophthalmic device 100F is also referred to as an IOL 100F. The IOL 100F is analogous to the IOL 100A. Consequently, analogous components have similar labels. Thus, the IOL 100F includes an optic 110 and closed-loop ring haptic structure 120F that are analogous to the optic 110 and closed-loop ring haptic structure 120A. Because optic 110 of IOL 100F is substantially the same as the optic 110 of IOL 100A, the optic 110 of IOL 100F will not be separately described with regard to FIG. 6A-6B. For clarity, FIGS. 6A and 6B are not to scale and not all components may be shown.

Like the closed loop haptic structure 120A of IOL 100A, the closed-loop haptic structure 120F of IOL 100F may include a first (inner) ring 122F, a second (outer) ring 124F, and connectors 126F-1, 126F-2, 126F-3, and 126F-4 (collectively labeled 126F).

The primary difference between IOL 100F and IOL 100A (described above) is that, in IOL 100F, the optic 110 and first ring 122F are located in a first plane substantially perpendicular to the optical axis 112 while the second ring 124F is located in a second plane substantially perpendicular to the optical axis 112. In certain embodiments, the first and second planes are spaced apart by at least one millimeter and not more than five millimeters. In certain embodiments, the first and second planes are spaced apart by nominally four millimeters. In the depicted embodiment, the first plane is posterior of the second plane, but that need not be the case. Additionally, because connectors 126F connect components located in different planes, the connectors 126H have components extending in both the radial and axial directions.

For substantially the same reasons as discussed above with regard to IOL 100A, IOL 100E may improve patient outcomes by reducing incidence of PCO. Additionally, IOL 100F may stretch the capsular bag in the axial direction as well the radial direction, which may improve stability and, as a result, refractive outcomes.

Figure 7A:
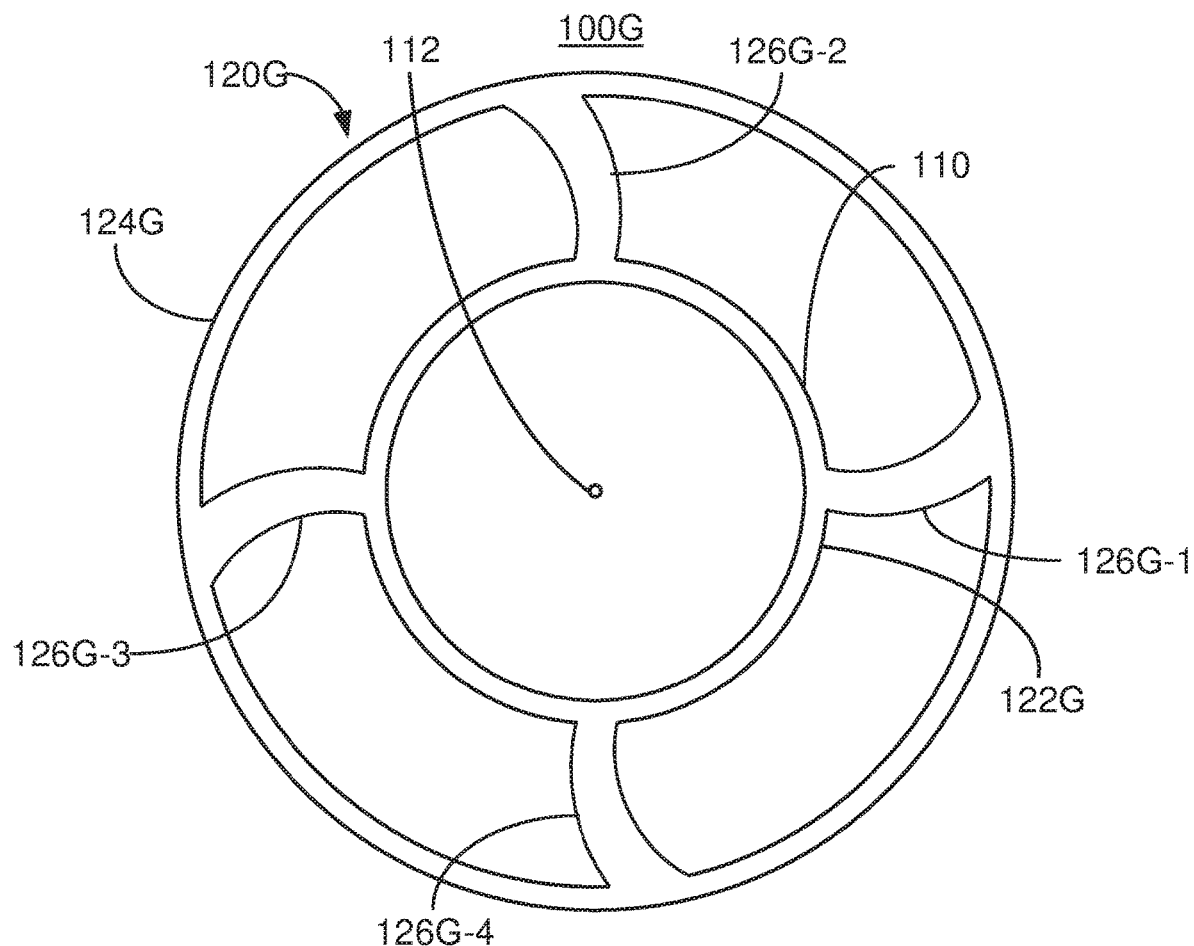
FIGS. 7A-7B depict various views of another exemplary embodiment of an ophthalmic device having a closed-loop ring haptic structure.
Figure 7B:
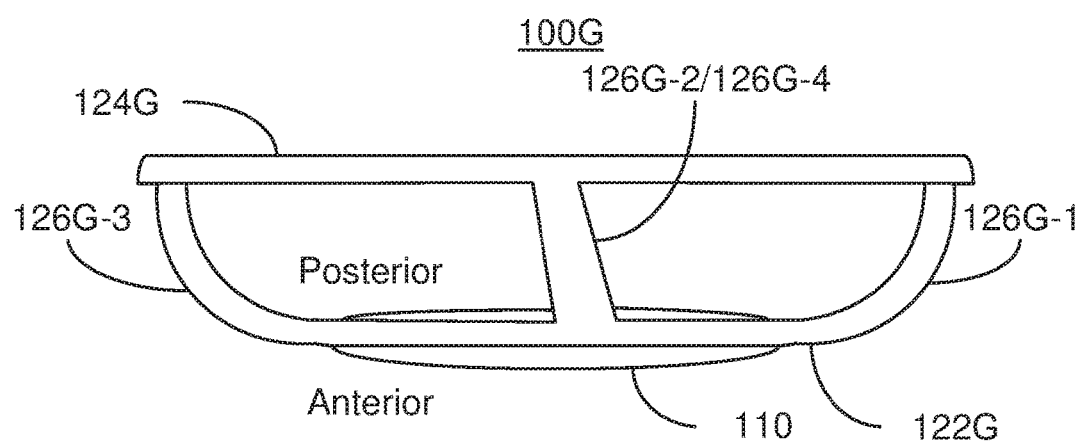

FIGS. 7A and 7B depict plan and side views, respectively, of another exemplary embodiment of an ophthalmic device 100G having an optic 110 and a closed-loop ring haptic structure 120G. For simplicity, the ophthalmic device 100G is also referred to as an IOL 100G. IOL 100G is substantially similar to IOL 100F except that connectors 126G are curved. In other words, each of the connectors 126G has a component in the axial direction, a component in the radial direction to connect the rings 122G and 124G, and a component perpendicular to the radial direction (i.e. in an angular direction around the circle). IOL 100G may improve patient outcomes for substantially the same reasons as discussed above with regard to IOL 100F.

Figure 8A:
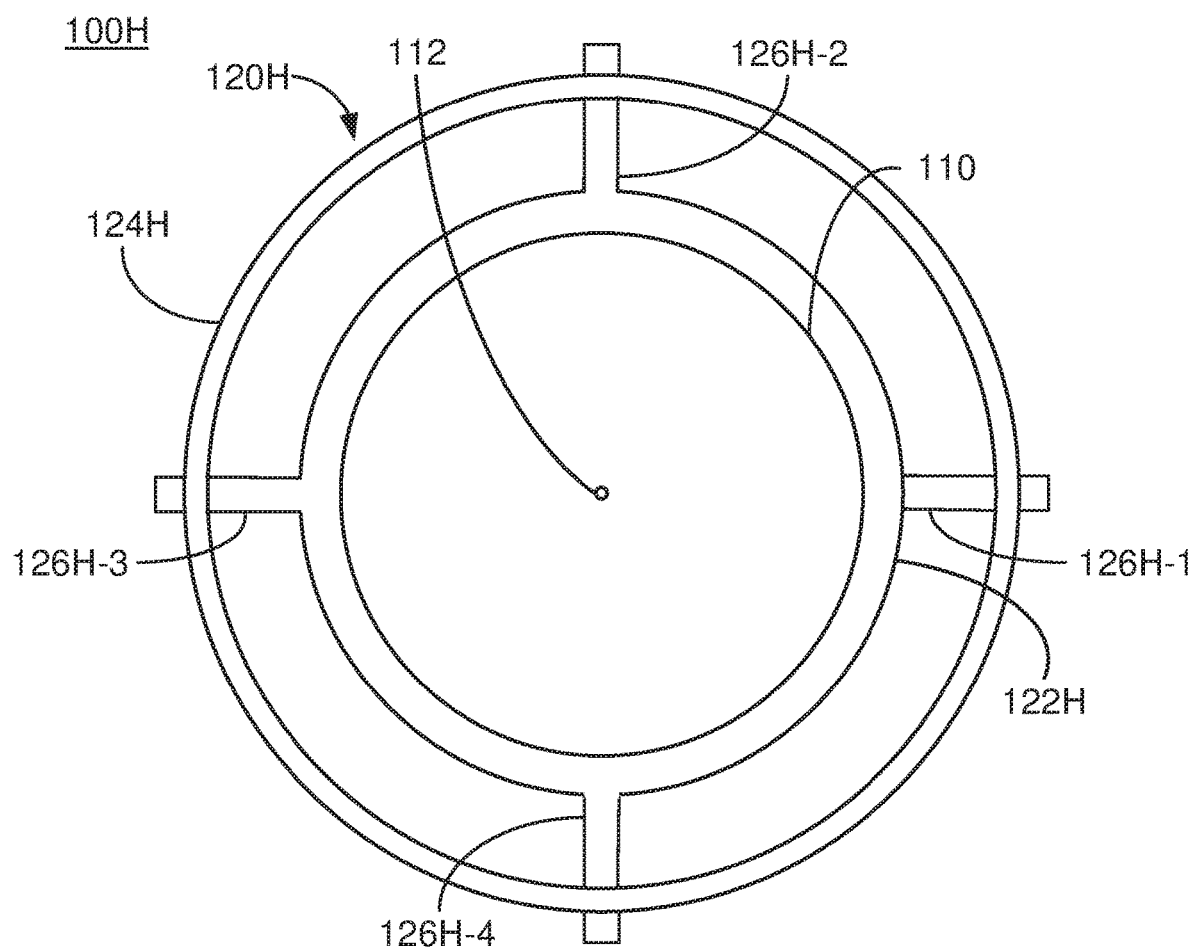
FIGS. 8A-8B depict various views of another exemplary embodiment of an ophthalmic device having a closed-loop ring haptic structure.
Figure 8B:
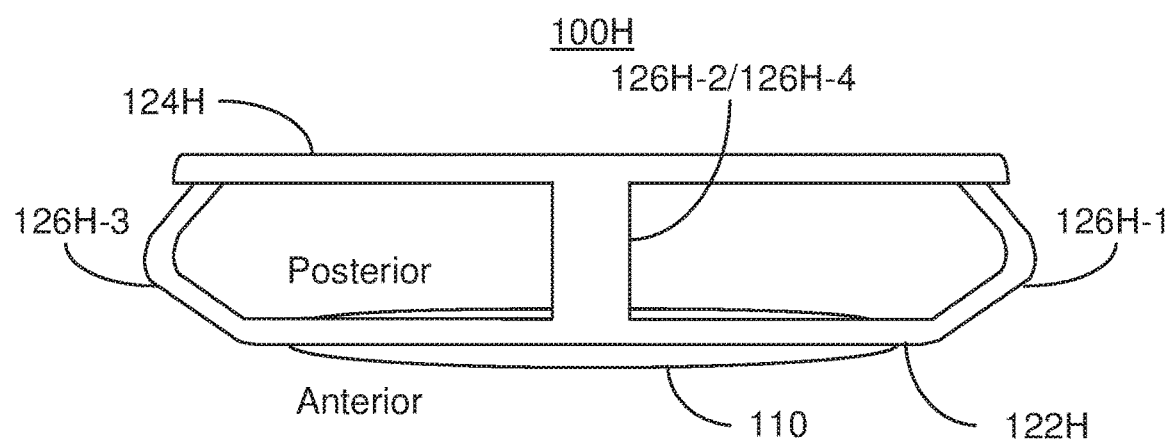

FIGS. 8A and 8B depict plan and side views, respectively, of another exemplary embodiment of an ophthalmic device 100H having an optic 110 and a closed-loop ring haptic structure 120H. For simplicity, the ophthalmic device 100H is also referred to as an IOL 100H. IOL 100H is substantially similar to IOL 100F except that connectors 126H have a bend between the first ring 122H and the second ring 124H. IOL 100H may improve patient outcomes for substantially the same reasons as discussed above with regard to IOL 100F. Additionally, the connectors 126H may be more likely to flex at the bend in response to compression, making movement of the optic 110 and/or closed-loop ring haptic structure 120H more predictable. As a result, refractive outcomes may be further improved.

It will be appreciated that various of the above-disclosed and other features and functions, or alternatives thereof, may be desirably combined into many other different devices or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An ophthalmic device comprising:
an optic including an optic axis and a periphery; and
a closed-loop ring haptic structure coupled with the optic and including a first ring having a first characteristic length, a second ring having a second characteristic length, and a plurality of connectors coupling the first ring and the second ring, wherein:
the first ring is positioned adjacent to the periphery of the optic and is coupled to the entire periphery of the optic; and
the first characteristic length is less than the second characteristic length; and
each of the plurality of connectors is curved such that each of the plurality of connectors includes a first component extending in a substantially radial direction and a second component extending in a direction substantially perpendicular to the radial direction in the same axial plane as the first component.

2. The ophthalmic device of claim 1, wherein the second ring further includes a third characteristic length.

3. The ophthalmic device of claim 2, wherein the first ring includes a plurality of apertures.

4. The ophthalmic device of claim 1, wherein:
the optic and the first ring are located in a first plane that is substantially perpendicular to the optical axis; and
the second ring is located in a second plane that is substantially perpendicular to the optical axis.

5. The ophthalmic device of claim 4, wherein the first plane is posterior of the second plane.

6. The ophthalmic device of claim 4 wherein each of the plurality of connectors includes a component extending parallel to the optical axis.

7. The ophthalmic device of claim 1, wherein at least one of the plurality of connectors comprises a plurality of struts.

8. The ophthalmic device of claim 1, wherein the plurality of connectors comprises a first set of ring structures connected to the first ring and a second set of ring structures connected to the second ring.

9. The ophthalmic device of claim 1, wherein the second ring comprises a plurality of apertures, such that the thickness of the second ring along the optical axis varies with radial position around the optic.

10. An ophthalmic device comprising:
an optic including an optic axis and a periphery; and
a closed-loop ring haptic structure coupled with the optic and including a first ring having a first characteristic length, a second ring having a second characteristic length, and a plurality of connectors coupling the first ring and the second ring, wherein:
the first ring is positioned adjacent to the periphery of the optic and is coupled to the entire periphery of the optic;
the first characteristic length is less than the second characteristic length; and
the plurality of connectors comprises a first set of ring structures connected to the first ring and a second set of ring structures connected to the second ring.

11. An ophthalmic device comprising:
an optic including an optic axis and a periphery; and
a closed-loop ring haptic structure coupled with the optic and including a first ring having a first characteristic length, a second ring having a second characteristic length, and a plurality of connectors coupling the first ring and the second ring, wherein:
the first ring is positioned adjacent to the periphery of the optic;
the first characteristic length is less than the second characteristic length; and
the first ring includes a plurality of apertures surrounded by portions of the first ring.

* * * * *